United States Patent
Lüdtke et al.

(10) Patent No.: US 11,293,035 B2
(45) Date of Patent: Apr. 5, 2022

(54) PROCESS FOR PRODUCING BIOGAS FROM FIBROUS SUBSTRATE

(71) Applicant: VERBIO VEREINIGTE BIOENERGIE AG, Leipzig (DE)

(72) Inventors: Oliver Lüdtke, Markkleeberg (DE); Michael Schlimbach, Halle/Saale (DE)

(73) Assignee: VERBIO VEREINIGTE BIOENERGIE AG, Leipzig (DE)

( * ) Notice: Subject to any disclaimer, the term of this patent is extended or adjusted under 35 U.S.C. 154(b) by 0 days.

(21) Appl. No.: 16/464,985

(22) PCT Filed: Nov. 30, 2016

(86) PCT No.: PCT/EP2016/079215
§ 371 (c)(1),
(2) Date: May 29, 2019

(87) PCT Pub. No.: WO2018/099547
PCT Pub. Date: Jun. 7, 2018

(65) Prior Publication Data
US 2019/0292569 A1  Sep. 26, 2019

(51) Int. Cl.
| | | |
|---|---|---|
| C12P 5/02 | (2006.01) | |
| C12M 1/107 | (2006.01) | |
| C02F 11/04 | (2006.01) | |

(52) U.S. Cl.
CPC ............ C12P 5/023 (2013.01); C02F 11/04 (2013.01); C12M 21/04 (2013.01); *C12P 2201/00* (2013.01); *Y02E 50/30* (2013.01)

(58) Field of Classification Search
None
See application file for complete search history.

(56) References Cited

U.S. PATENT DOCUMENTS

| | | | | |
|---|---|---|---|---|
| 2006/0175252 A1* | 8/2006 | Upendrakumar | ....... | C02F 3/286 210/603 |
| 2012/0058534 A1* | 3/2012 | Stover | ..................... | C02F 3/286 435/167 |
| 2013/0164795 A1* | 6/2013 | Lowe | ....................... | C12P 7/16 435/134 |
| 2016/0214879 A1* | 7/2016 | Josse | ....................... | C02F 11/04 |

FOREIGN PATENT DOCUMENTS

| | | | |
|---|---|---|---|
| WO | WO 2010/094115 A1 | 8/2010 | |
| WO | WO-2010094115 A1 * | 8/2010 | ............ C12M 21/04 |
| WO | WO 2013/155631 A1 | 10/2013 | |
| WO | WO 2015/092003 A1 | 6/2015 | |

OTHER PUBLICATIONS

Yi, Jing et al., "Effect of Increasing Total Solids Contents on Anaerobic Digestion of Food Waste under Mesophilic Conditions: Performance and Microbial Characteristics Analysis", PLos One, vol. 9, No. 7, Jul. 2014 (Jul. 2014), XP002767355, 10pp.

DHV Consultants BV & Delft Hydraulics, "Training module # WQ-10 How to measure dissolved, suspended & total solids", Nov. 2, 2002, 29pp.

* cited by examiner

*Primary Examiner* — Nghi V Nguyen
(74) *Attorney, Agent, or Firm* — Lewis Roca Rothgerber Christie LLP

(57) ABSTRACT

The invention relates to a process for producing biogas from fibrous substrate by anaerobic fermentation. The process is characterised in that
a) the fibrous substrate is fed together with process liquid to a fermenter containing anaerobic microorganisms depending on the TSS content ascertained in this fermenter,
b) the fibrous substrate is subjected to wet fermentation in this fermenter to produce biogas
c) the output containing fermented fibrous substrate is drawn off from the fermenter and the TSS content in the fermenter is ascertained,
d) the TSS content ascertained is compared with a fixed target range and
e) depending on the result from d), step a) is repeated with adjusted amounts in order to comply with the target range for the TSS in the fermenter.

9 Claims, 1 Drawing Sheet

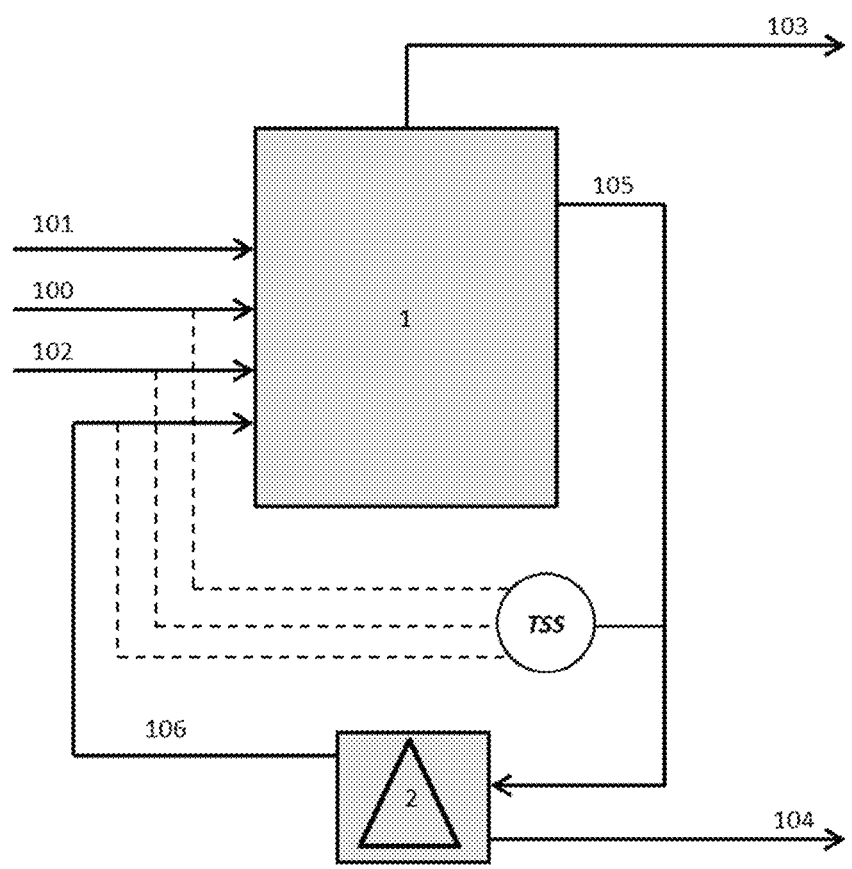

PROCESS FOR PRODUCING BIOGAS FROM FIBROUS SUBSTRATE

CROSS-REFERENCE TO RELATED APPLICATION(S)

This application is a National Phase Patent Application of International Patent Application Number PCT/EP2016/079215, filed on Nov. 30, 2016. The entire content of which is incorporated herein by reference.

The invention relates to a process for producing biogas from fibrous substrate by anaerobic fermentation.

DESCRIPTION OF THE PRIOR ART

The breakdown of organic substrate by microbial anaerobic processes, also referred to as fermentations, is known. In the production of biogas (a mixture predominantly of methane and carbon dioxide), the organic substrate is broken down in a number of stages (hydrolysis, acidification and methane formation). The used substrate is an organic substance or a mixture of various organic substances. Depending on the substrate and desired product, certain microorganisms or groups of microorganisms are suitable for the fermentation process. For fermentation to be performed successfully, it must be ensured, in addition to the substrate supply, that nutrients are also supplied, and that favourable process parameters such as temperature and pressure are provided. The organic substrate is broken down anaerobically to varying degrees of efficacy depending on the composition. Simple molecules and carbohydrates, proteins and lipids can be broken down very well. Macromolecules of fibre constituents, such as hemicellulose and cellulose and lignin, are more difficult to break down anaerobically, or cannot be broken down anaerobically at all. The fibre constituents that cannot be broken down are removed from the process.

Biogas production has gained increasingly in importance in recent years. Whereas the anaerobic treatment of sewage sludge was primarily focused on the objective of sludge reduction with formation of biogas, the focus more recently has been on the recovery of biogas from agricultural cultivated biomass, such as whole crop silage, sometimes also combined with the fermentation of manure or other livestock excrements. Focus has been placed increasingly on the production of biogas from agricultural waste materials, since these have no food or feed competition. However, the agricultural waste materials are generally fibre-containing substrates, which are therefore more difficult to breakdown. For high profitability, the highest possible biogas yield in relation to the fibrous organic substrate used is necessary. There are a range of technical proposals which aim to achieve this objective.

Prior art techniques for achieving high biogas yields include a moderate, uniform substrate feed and a sufficient supply of macro- and micronutrients and also the provision of the longest possible dwell time of the substrate in the fermentation process. Here, with regard to the economic efficiency of a facility, a compromise must be made between high volumetric loading and long dwell time and thus associated high biogas yield. Usually, the compromise lies in increasing the facility outputs until the process quality drops measurably or the process stability decreases.

In the fermentation of fibrous substrate, the limiting factor is generally the miscibility or the actual viscosity in the fermenter. Due to the high fibre content, hydrolysis is the limiting breakdown process.

It is known to a person skilled in the art that the viscosity of the fermenter content increases significantly from certain dry substance contents (TS). The mixing and therefore the convective material transport and, ultimately, the biogas formation is thus hindered considerably. Very different values for maximum possible TS contents are specified in the specialist literature for wet fermentation. For example, a typical limit of 12% is stated for wet fermentation in "Leitfaden Biogas" ("The Biogas Handbook") (ISBN 3-00-014333-5, 6th edition, 2013)

It is also stated in "Leitfaden Biogas" that there are no precisely defined limits for the different substrates:

"In wet fermentation processes, dry substance contents of up to 12 mass % have been encountered in the fermenter liquid. A limit of 15 mass % constitutes a general rule of thumb for the pumpability of the medium, however this value should be considered qualitatively and is not considered representative for all feedstocks. Some substrates with a finely dispersed particle distribution and high contents of dissolved substances are also still pumpable at TS contents of up to 20 mass %, for example dispersed food waste from the tanker. By contrast, other substrates are present in stackable form already at 10 to 12 mass %, for example fruit and vegetable peel."

The invention addresses in particular the problem of providing a process concept for efficient and economical production of biogas from any fibrous substrate.

SUMMARY OF THE INVENTION

The problem is solved or at least mitigated by a process for producing biogas from fibrous substrate by anaerobic fermentation. according to claim 1, which process comprises the following steps:

a) a fibrous substrate is fed together with process liquid to a fermenter containing anaerobic microorganisms depending on the TSS content ascertained in this fermenter, b) biogas is produced from the fibrous substrate in this fermenter by wet fermentation, c) the output containing fermented fibrous substrate is drawn off from the fermenter and the TSS content is ascertained, d) the TSS content ascertained is compared with a fixed target range, and e) the feed of the fibrous substrate and/or process liquid is adapted.

In this application, "fibrous substrate" is understood to mean substrates without significant amounts of free water and with a significant content of fibre constituents, such as lignocellulose fibres. This includes for example, but not exclusively, hay or grasses from landscaping, straw, or other waste materials from grain production, rape straw, pea straw, miscanthus, reed canary grass, millet or other whole energy crops or crop parts or fibrous industrial waste materials, for example from the wood-processing industry.

In the sense of this application, biogas includes any gas formed microbially within the scope of a single-stage and/or multi-stage fermentation. Biogas contains primarily $CO_2$, methane and/or hydrogen and water, and also, depending on the substrate and fermentation process, ammonia and hydrogen sulphide.

The suspended dry substance (TSS) describes the particulate proportion of the dry substance (TS). In the case of fibrous media, the TSS is determined substantively by the fibre content of the medium. The TSS, together with the dissolved dry substance, gives the total dry substance. Depending on the analysis method, very small particles below the separation size of the analysis method are allocated to the dissolved dry substance.

In a preferred embodiment the process according to the invention is configured such that the TSS content is the fibre content.

In a further preferred embodiment the process according to the invention is configured such that the fibrous substrate is fed together with process liquid, such that a TSS content in the fermentation medium between 4% and 10%, preferably between 5% and 8%, particularly preferably between 6 and 7% is given.

In a further preferred embodiment the process according to the invention is configured such that the fibrous substrate is fed together with process liquid, such that a fibre content in the fermentation medium between 4% and 10%, preferably between 5% and 8%, particularly preferably between 6 and 7% is given.

In a further preferred embodiment the process according to the invention is configured such that nutrients and trace elements are fed directly or indirectly to the fermentation process.

In a further preferred embodiment the process according to the invention is configured such that the fermenter content is stirred during fermentation.

In a further preferred embodiment the process according to the invention is configured such that the output is subjected to a solid-liquid separation, and during this separation moist fibrous fermentation residue and a process liquid are produced.

In a further preferred embodiment the process according to the invention is configured such that the process liquid produced in a solid-liquid separation is fed back to a fermenter.

In a further preferred embodiment the process according to the invention is configured such that fresh water is fed to a fermenter.

In a further preferred embodiment the process according to the invention is configured such that pumpable fermentable substrate is used as process liquid.

In a further preferred embodiment the process according to the invention is configured such that the fibrous substrate is ground prior to the fermentation.

In a further preferred embodiment the process according to the invention is configured such that the TSS content is determined in accordance with the following method, in which:

a) aliquots of an output sample are provided for various analyses, b) the total TS content of this sample is measured from an aliquot, c) another aliquot of this sample is firstly centrifuged and fine-filtered, and the TS content is determined from the filtrate, and d) the TSS content is calculated from the total TS content of the output and the TS content of the filtrate.

The process according to the invention also relates in particular to all combinations of the above-described, preferred embodiments.

Biogas is produced from fibrous substrate particularly expediently and economically in a single-stage process. Here, all breakdown steps are performed in parallel in a mixed fermenter. Multi-stage fermentation processes are also possible, in which for example a primary fermentation and secondary fermentation takes place or a plurality of fermenters are operated in parallel.

Biogas can also be produced by decoupling the breakdown steps into a hydrolysis process and a fermentation process. Predominantly the hydrolysis and acidification of the substrate then take place in the hydrolysis reactor. The methane formation then takes place in the subsequent fermentation process, such that the gas formed in this reactor contains the predominant portion of the methane formed from the substrate.

A very good mixing is achieved in the case of a hydrolysis or fermentation in the wet fermentation process if the fibrous substrate is mixed with process liquid to form a suspension.

The fibrous substrate is fed in the form of a suspension to an anaerobic fermentation process following a comminution together with the process liquid as appropriate. The comminution is performed expediently to particle sizes ranging from 1 mm to 20 mm, preferably ranging from 2 mm to 15 mm, particularly preferably ranging from 3 mm to 10 mm, very particularly preferably ranging from 4 mm to 6 mm.

The anaerobic breakdown of the organic substance into biogas takes place in a fermenter containing anaerobic microorganisms preferably under continuous stirring in order to improve the material exchange. If, by the fed substrates, there is an insufficient supply of nutrients and trace elements, these are fed suitably to the fermentation process.

Whereas part of the TS is broken down to form biogas, another part is broken down into soluble constituents, and a further part of the substrate (for example fibre constituents) is not subject to any breakdown, or is only subject to a small breakdown, and remains in the form of suspended TS in the fermentation medium. Lignin compounds in particular are subject to almost no anaerobic breakdown at all.

In order for the biogas formation to be as efficient as possible, it is necessary to achieve the highest possible substrate concentrations in the fermenter. The dwell time in the fermenter is thus maximised, and a high utilisation of space, based on the fermenter volume, is achieved. At the same time, the substrate concentration must not be increased to such an extent that the viscosity of the fermentation medium rises in such a way, due to a high TS content, that sufficient mixing can no longer be ensured.

The viscosity of a particulate fermentation medium is difficult to measure, and it is almost impossible to correlate the measurement result with the quality of the mixing. The TS content may also reflect the miscibility only insufficiently, since it is composed of different fractions (for example dissolved and suspended TS), which act to varying degrees on the mixing properties of the fermentation medium.

It has been found that the suspended TS (TSS) is a very well-suited measurand for controlling the substrate feed in the biogas process. Whereas dissolved TS plays a subordinate role for miscibility, the influence of the TSS is dominant. Surprisingly, it has been found that the content of dissolved TS does not have any influence on the yield for the fermentation of fibrous substrate.

The TSS in the fermentation medium can be determined by suitable methods and is thus known for the entire fermenter content. It is thus possible, also with different substrate composition, to place the capacity of the fermenter always in the optimal range by adapting the substrate feed and/or feed of the process liquid. Here, it is advantageous, but not absolutely necessary, if the TS composition of the substrate and the process liquid are also known.

In some applications it may be helpful, instead of the TSS, to use the fibre content of the fermentation medium as a controlled variable. The fibre content can be determined by different methods, for example as raw fibre content on the basis of a Weende analysis. The use of ADF or ADL values from an extended Weende analysis as fibre content is also possible.

The process liquid can consist of liquid and/or water obtained from within the process. In particular, particulate constituents above the separation size of the particular separation process can be separated from the fermentation medium by a solid-liquid separation. The resultant process liquid can be used once more for the mixing of new substrate, or can be fed back into the fermenter.

It has surprisingly been found in tests that a substrate-independent limit value for the suspended dry substance in the fermentation medium, at which limit value the biogas formation is optimal, exists for a certain fermentation system consisting of a fermenter and the associated staring equipment. Above this limit value, a lack of mixing may lead to a local overload of the biology and thus to an acid accumulation in the fermentation medium. A further effect is the reduction of the gas yield.

It has been found that the biogas formation is optimal when a TSS content in the fermentation medium between 4% and 10%, preferably between 5% and 8%, particularly preferably between 6 and 7% is provided.

The control concept is applicable also for a multi-stage approach, for example with primary fermentation and secondary fermentation or with fermentations operated in parallel. In these cases, each individual fermenter may be subject to a control process. The control concept can also be applied in the case of multi-stage processes with hydrolysis and downstream primary fermentation.

Further advantageous developments of the invention can be inferred from the dependent claims or the following description.

BRIEF DESCRIPTION OF THE DRAWINGS

FIG. 1 shows a flow diagram of the test structure of Example 3

DETAILED DESCRIPTION OF THE INVENTION

Example 1

The determination of the TSS is described in detail hereinafter.

Principle: The dry substance and the dissolved dry substance of a sample are determined by evaporating water of an undiluted sample or a diluted filtrate in a muffle furnace. The suspended dry substance (TSS) can be calculated using these values.

Material: 50 ml centrifuge tube, disposable syringe 5 ml, syringe preliminary filter 0.2 μm, analytical balance, centrifuge, Nabertherm B180 muffle furnace, refractory glass dish, desiccator, crucible tongs, distilled water.

Execution: The determinations of the dry substance and the dissolved dry substance are to be performed as double determinations. The sample to be examined is homogenised by shaking prior to its removal. For the TS determination, dishes are weighed and in each case the weight (m1) is noted. 10.00±1.0 g of the sample are filled into each dish and the end weight is likewise noted (m2). In order to determine the dissolved dry substance, 10.00±1.0 g of sample are weighed into a 50 ml centrifuge tube, and the exact masses noted (m4). Distilled water is added to 50.00 g±1.0 g and the total mass is noted (m5). The content of the tube is homogenised by shaking and centrifuged at 4,400 r for 5 min. Each dish is weighed and the weight is noted (m6). 10.00 g±1.0 g of the centrifuge is added to each dish via a 0.2 μm preliminary syringe filter. The end weight is noted (m7). All of the dishes are placed in the muffle furnace with the aid of crucible tongs in order to evaporate the water. The dishes are heated by 5° C./min to 105° C. and, once the temperature is reached, it is maintained for three hours. The samples are then placed in the desiccator for approximately 20-30 min for cooling. After the cooling the dishes are weighed and the mass noted (mass of the sample for the TS determination m3, mass of the sample for the dissolved TS determination m8). The dry substance TS and the dissolved dry substance TSgel. are calculated on the basis of the formulas stated below. The suspended dry substance TSS can be calculated from the difference between the value for the dry substance and the value for the dissolved dry substance. If the evaluation indicates a content of less than 1% for the diluted dissolved TS content TS*gel., the determination must be repeated with a smaller dilution.

Calculation:

Dilution factor DF for the sample weigh-in:

$$DF = m5/m4$$

m4 mass of the sample m5 total mass after dilution

The content of dry substance of the initial sample is calculated by:

$$TS = (m3-m1)/(m2-m1)$$

m1 empty mass of the crucible of the TS determination m2 mass of the full crucible of the TS determination before 105° C.

m3 mass of the crucible of the TS determination after 105° C.

The dissolved dry substance of the diluted sample TS*gel. is calculated by:

$$TS^*gel. = (m8-m6)/(m7-m6)$$

m6 empty mass of the crucible of the TSgel. determination m7 mass of the full crucible of the TSgel. determination before 105° C.

m8 mass of the crucible of the TSgel. determination after 105° C.

The value for the dissolved dry substance TSgel. corrected by the suspended dry substance TSS can be determined by the following equation:

$$TSgel. = DF^*(TS^*gel.^*(1-TS/DF))/(1-TS^*gel.)$$

TS*gel. determined dissolved dry substance in the diluted sample

TS dry substance of the sample

The difference between dry substance TS and dissolved dry substance TSgel. is the suspended dry substance TSS:

$$TSS = TS - TSgel.$$

Example 2

A further method for determining the TSS content is described in detail hereinafter.

The TSS is determined by vacuum filtration of a defined sample quantity through a cellulose acetate filter with a pore size of 0.45 μm.

The 0.45 μm cellulose acetate filter can be prewashed with 150 ml water in order to remove the water-soluble contaminations. The filter is then dried at 105° C. for at least one hour to constant mass and stored in the desiccator until use. It should be noted that the filter is not contaminated by dust.

The filter is weighed prior to the filtration (m1) and is then placed in the funnel of a filtering unit.

The sample to be examined is homogenised by vigorous shaking, and then approximately 10 g (m2) of this sample are filled directly into a 25 ml measuring cylinder. The sample is filtered by means of vacuum, and the measuring cylinder is flushed twice with 25 ml water. The filter and the funnel are then flushed with a further 50 ml water, and the filter is sucked dry. The subsequent drying of the filter is performed at 105° C. in a drying cabinet to constant mass (m3). The TSS can be calculated from the end weight via the following equation.

m1 mass of the unloaded filter
m2 sample weigh-in
m3 mass of the loaded filter after filtration $$TSS = (m3 - m1)/m2$$

Example 3

The possibility of a technical execution of the process will be explained hereinafter on the basis of the fermentation of straw. Merely by way of example, straw represents the fibrous substrates considered in this application. The details are readily transferable by a person skilled in the art to the use of other suitable substrates.

The example makes reference to FIG. 1, in which the reference signs have the following meanings:
100 straw
101 nutrients/trace elements
102 water
103 biogas
104 waste material
105 output
106 process liquid
1 fermentation
2 solid-liquid separation Straw, as an agricultural waste material, is very well suited as a substrate for biogas recovery. However, straw contains significant amounts of substances which are difficult to breakdown and which are hardly, or not at all, broken down within economically reasonable time periods. The substrate composition can vary greatly depending on the type of straw and the time of harvesting and also storage conditions. Rape straw in Germany, for example, has a moisture of approximately 30%, whereas wheat straw, if the weather is dry and if stored properly, usually contains only approximately 90% moisture. Rice straw by comparison contains a particularly large amount of mineral substances and can contain crude ash contents of more than 20% of the TS.

Typical ranges of some of the contents of straw are shown in the following table:

|  | Min | Max |
| --- | --- | --- |
| Moisture | 5% of the OS | 40% of the OS |
| TS | 60% of the OS | 95% of the OS |
| oTS | 75% of the TS | 97% of the TS |
| Crude ash | 3% of the TS | 25% of the TS |
| lignin (ADL) | 3% of the TS | 20% of the TS |
| nitrogen (Kjeldahl) | 0.3% of the OS | 1.1% of the OS |

Depending on the straw type and quality, the biogas potential can differ significantly. The dry substance remaining in the fermentation process following breakdown of the substance capable of being broken down can also differ significantly. In the case of rice straw for example a significant proportion of dry substance is retained after the fermentation due to the high mineral substance content. However, at the same time, a significant proportion of the mineral substances is converted into dissolved dry substance. This proportion is of subordinate importance for the mixing behaviour of the fermentation medium.

Biogas tests were performed in a test facility consisting of a continuous stirrer tank (fermenter, 1). The schematic structure can be seen in FIG. 1. Once the system had been started with inoculum, water and wheat straw as substrate, with feed of nutrients and trace elements, quasi-continuous operation was provided thereafter with constant fill level with the same batch of wheat straw. Output (105) was drawn off daily from the system, and fresh, ground straw (100) and also process liquid (106) and water (102) were fed. The nutrient and trace element feed (101) was performed at regular intervals.

A small part of the output (105) was analysed. The majority of the output (105) was subjected to a solid-liquid separation in a decanter (2). A pourable fibrous fermentation residue (104) and a process liquid (106) were thus obtained. The obtained process liquid (106) was passed back into the fermenter (1). In addition to the process liquid (106), 15% fresh water (102) was also used.

In the stationary state, a TSS content of 6.5% was provided in the fermentation medium. The content of dissolved dry substance at this point in time was 2.0%.

In further tests the TS content in the fermentation medium was increased by increased substrate feed and proportional reduction of the water feed. At TS contents above 8.5%, in particular above 9%, and an associated rise in the TSS content to values above approximately 6.8%, there was an accumulation of acetic acid in the fermentation medium, which was attributed to a significantly hindered mixing. It was possible to determine by means of inspection glasses that only local mixing was still provided in the immediate vicinity of the agitator at such a high TSS content, whereas, with a TSS content of 6.5%, mixing over a large volume was observed in the fermentation medium.

By changing the substrate to rice straw with a crude ash content of approximately 20% of the TS (instead of 7% of the TS in the case of wheat straw), a significantly greater amount of TS not able to be broken down remained in the system. The fermentation process was initially performed such that a uniform TS content of approximately 8.5% was provided in the fermentation medium. This was possible only by a lower substrate feed in comparison to wheat straw.

On the basis of measured values in the output, it was determined that the TSS content in the fermentation medium decreased continuously after the substrate change, whereas the content of dissolved TS increased. The feed of rice straw was then increased, and the feed of process liquid adapted such that a TSS of 6.5% was again produced in the fermentation medium. The proportion of dissolved TS increased accordingly, with the use of rice straw, to approximately 3.0%, and therefore the total content of TS in the fermentation medium increased to 9.5%. Stable operation alongside such a high TS was not possible in the case of wheat straw.

Similarly to that experienced already in the previous test with wheat straw, a further increase of the contents of TSS or TS led to an accumulation of acetic acid as a result of a deteriorating mixing.

in further tests, the control concept was also confirmed for other substrates.

The invention claimed is:

1. A process for producing biogas from fibrous substrate by anaerobic fermentation, characterised in that
   a) the fibrous substrate is fed together with process liquid to a fermenter containing anaerobic microorganisms, the amount of the fibrous substrate and of the process liquid fed to the fermenter depending on a suspended dry substance (TSS content) ascertained in this fermenter,
   b) the fibrous substrate is subjected to wet fermentation in this fermenter to produce biogas,
   c) an output containing fermented fibrous substrate is drawn off from the fermenter and the TSS content in the fermenter is ascertained,
   d) the TSS content ascertained is compared with a fixed target range between 4% and 10%,
   e) the output of step c) is subjected to a solid-liquid separation, and in so doing moist fibrous fermentation residue and the process liquid are produced, and
   f) depending on the result from d), step a) is repeated with adjusted amounts in order to comply with the fixed target range for the TSS content in the fermenter.

2. The process according to claim 1, characterised in that the TSS content is a fibre content.

3. The process according to claim 1, characterised in that the fibrous substrate is fed together with the process liquid, such that the TSS content in a fermentation medium in the fermenter between 4% and 10% is given.

4. The process according to claim 1, characterised in that the fibrous substrate is fed together with the process liquid, such that a fibre content in a fermentation medium in the fermenter between 4% and 10% is given.

5. The process according to claim 1, characterised in that a content in the fermenter is stirred during the wet fermentation.

6. The process according to claim 1, characterised in that the process liquid produced in the solid-liquid separation is fed back to the fermenter.

7. A process for producing biogas from fibrous substrate by anaerobic fermentation, characterised in that
   a) the fibrous substrate is fed together with process liquid to a fermenter containing anaerobic microorganisms, the amount of the fibrous substrate and of the process liquid fed to the fermenter depending on a suspended dry substance (TSS content) ascertained in this fermenter,
   b) the fibrous substrate is subjected to wet fermentation in this fermenter to produce biogas,
   c) an output containing fermented fibrous substrate is drawn off from the fermenter and the TSS content in the fermenter is ascertained,
   d) the TSS content ascertained is compared with a fixed target range between 5% and 8%,
   e) the output of step c) is subjected to a solid-liquid separation, and in so doing moist fibrous fermentation residue and the process liquid are produced, and
   f) depending on the result from d), step a) is repeated with adjusted amounts in order to comply with the fixed target range for the TSS content in the fermenter.

8. A process for producing biogas from fibrous substrate by anaerobic fermentation, characterised in that
   a) the fibrous substrate is fed together with process liquid to a fermenter containing anaerobic microorganisms, the amount of the fibrous substrate and of the process liquid fed to the fermenter depending on a suspended dry substance (TSS content) ascertained in this fermenter,
   b) the fibrous substrate is subjected to wet fermentation in this fermenter to produce biogas,
   c) an output containing fermented fibrous substrate is drawn off from the fermenter and the TSS content in the fermenter is ascertained,
   d) the TSS content ascertained is compared with a fixed target range between 6% and 7%,
   e) the output of step c) is subjected to a solid-liquid separation, and in so doing moist fibrous fermentation residue and the process liquid are produced, and
   f) depending on the result from d), step a) is repeated with adjusted amounts in order to comply with the fixed target range for the TSS content in the fermenter.

9. The process according to claim 1, characterised in that the fibrous substrate contains a dry substance content (TS) within the range of 60%-95%.

* * * * *